United States Patent [19]
Bohn et al.

[11] 3,957,975
[45] May 18, 1976

[54] USE OF THE PREGNANCY-SPECIFIC $\beta_1$-GLYCO-PROTEIN AND ITS ANTIBODY FOR CONTRACEPTION

[75] Inventors: Hans Bohn, Marbach, near Marburg an der Lahn; Ernst Weinmann, Michelbach, near Marburg an der Lahn, both of Germany

[73] Assignee: Behringwerke Aktiengesellschaft, Frankfurt and der Lahn, Germany

[22] Filed: Sept. 10, 1974

[21] Appl. No.: 504,700

[30] Foreign Application Priority Data
Sept. 12, 1973 Germany............................ 2345953

[52] U.S. Cl. .............................................. 424/177

[51] Int. Cl.² ................ A61K 37/00; C07C 103/52
[58] Field of Search ..................................... 424/177

[56] References Cited
OTHER PUBLICATIONS
Song et al.: Chem. Abstr. 73:127431d, (1970).

*Primary Examiner*—Lewis Gotts
*Assistant Examiner*—Reginald J. Suyat
*Attorney, Agent, or Firm*—Curtis, Morris & Safford

[57] ABSTRACT
Use of the pregnancy-specific $\beta_1$-glycoprotein (SP$_1$) and its antibody for contraception and for inducing miscarriages.

1 Claim, No Drawings

USE OF THE PREGNANCY-SPECIFIC $\beta_1$-GLYCO-PROTEIN AND ITS ANTIBODY FOR CONTRACEPTION The present invention relates to the use of the pregnancy-specific $\beta_1$-glycoprotein ($SP_1$) and its antibody for contraception and for inducing miscarriages.

Attempts have been made in which antisera against extracts of animal placentae were to prevent rabbits from conception and to induce miscarriages in monkeys and mice. Further attempts have been made to reduce the fertilisation rate of rats by the active immunisation with human placenta-lactogen. All these attempts did not reach beyond the commencing stage and, especially, were not used in medicine.

Now, it was found that the pregnany-specific $\beta_1$-glycoprotein which can be obtained from placentae or sera, and its antiserum can be used for contraception and induction of miscarriages in primates, for example, in human beings and in monkeys.

The $SP_1$ is a known compound which is present, for example in the blood of pregnant women. It belongs to the pregnancy-specific proteins and is probably formed in the syncytiotrophoblast of the placenta. It can be obtained, for example according to the process described in German Patent Application No. P 21 57 610.3 HOE 71/B 020, —Ma 141 a) from placentae or the serum or the urine of pregnant women. The $SP_1$ has not yet been used for contraception or for the induction of miscarriages.

The $SP_1$ can be used for contraception directly by active immunisation of the recipient. An effective amount of the $SP_1$ is administered to the recipient by injection, advantageously by several, temporaly graduated single injections, preferably by the intravenous route. The total dosage unit which is to be administered gradually by these single injections, is to be chosen depending on the weight of the recipient. It is several mg per kg or less, preferably about 0.2 to 10 mg per kg, so that a single injection has a dosage unit of a fraction of a mg up to 10 mg per kg of body weight of the recipient. The $SP_1$ is administered advantageously in the form of a solution in a physiologically acceptable liquid, such as an isotonic sodium chloride solution.

In addition to the active immunisation the $SP_1$ can also be used in the form of an antiserum for contraception. Heretofore, antisera are obtained in known manner from suitable testing animals, for example horse, cattle, goat or rabbit. From these antisera, the antibodies can be isolated by known methods, for example by salting out (for example by precipitation with ammonium sulfate) or by chromatographical methods (for example with DEAE cellulose, preferably as column). The antibodies can be lyophilised, if desired and are durable in this form over a period of several years. They are applied for passive immunisation in amounts of 50 – 500 mg per kg. body weight of the patient.

A special advantage of the use of the $SP_1$ is its immunological activity, which makes this compound superior to any physical or chemical measure. Side effects such as became known for the methods hitherto used, were not observed.

The following examples illustrate the invention:

EXAMPLE 1

Preparation of antisera and purification of the antibodies

40 Rabbits were immunised with the pregnany-specific $\beta_1$-glycoprotein. From the serum of the animals the anti-bodies were isolated by precipitating with $(NH_4)_2SO_4$ (30 % w/v) and by chromatography with DEAE cellulose and 0.04 molar phosphate buffer at pH 7. The antibodies passed through the column without hindrance, the other serum proteins remained linked to the DEAE cellulose. The eluate containing the antibodies was concentrated to 5 % protein, 2.25 % of glycin were added, it was filtered sterile, filled up in portions of 5 ml and lyophilised. Each portion contained 250 mg of protein.

EXAMPLE 2

Interruption of pregnancy

On sexually mature female monkeys of the species cynomolgus the cycle of the individual animal was determined by taking daily vaginal smears. At the date evaluated therefrom for the ovulation the female monkeys were brought together for 2 days with male animals. The proof of sperms in the vagina served as a control of the mating. 17, 18 and 19 days after the mating a serum sample was obtained and tested in the mouse test. Samples of most of the aimals were positive and indicated a pregnancy. Between the 30th and 40th day of pregnancy eight of the pregnant animals were administered by the intravenous route on three subsequent days each 250 mg of the antibody preparation from the rabbit serum against the pregnancy-specific $\beta_1$-glycoprotein (prepared according to Example 1), dissolved in 5 ml. Within a few days after the last injection the foetus was eliminated in all cases.

Two pregnant control animals that were treated in an analogous manner were administered a correspondingly prepared preparation which was obtained from normal rabbit serum and did not contain any antibodies against the human pregnancy-specific $\beta_1$-glycoprotein. They carried their youngs normally to full term and gave them birth alive.

EXAMPLE 3

Contraception with antiserum 5 sexually mature female monkeys were administered by intravenous injection 2 days before the calculated ovulation each time 250 mg of the antibody preparation from the rabbit serum against the pregnancy-specific $\beta_1$-glycoprotein (prepared according to Example 1). At the time of the ovulation they were brought together with male animals. The proof of sperms in the vagina served as control for the mating. 17, 18 and 19 days after the mating serum samples were obtained and tested in the mouse test. All the animals showed negative samples, the monkeys were not pregnant.

The sera of control animals that were not treated previously were positive in the mouse test. They gave their youngs birth alive.

EXAMPLE 4

Contraception by active immunisation

Two sexually mature female monkeys were actively immunised with pregnancy-specific $\beta_1$-glycoprotein by administering intravenously to each monkey in several portions at intervals of a few days a total of 4 mg of the pregnancy-specific $\beta_1$-glycoprotein — dissolved in physiologically acceptable sodium chloride solution. The immunisation took place over a period of time of 5 – 6 weeks. Thereafter, testing for antibodies against the pregnancy-specific $\beta_1$-glycoprotein followed. Both sera were positive.

2 days before the calculated ovulation and further 2 days before the following calculated ovulation dates the immunised monkeys were brought together for 5 days in each case with male animals.

17, 18 and 19 days after the mating a serum sample was tested in the mouse test. All samples were negative. No pregnancy had occurred.

Thus, the tests for mating during a prolonged period of time of the female monkeys pretreated with the pregnancy-specific $\beta_1$-glycoprotein did not show any results.

We claim:

1. Process for contraception or for inducing of miscarriages in primates which comprises parenterally administering to a primate an effective amount of an aqueous dispersion of the pregnancy-specific $\beta_1$-glycoprotein.

* * * * *